(12) United States Patent
Dijk et al.

(10) Patent No.: US 7,801,617 B2
(45) Date of Patent: Sep. 21, 2010

(54) AUTOMATIC MEASUREMENT OF NEURAL RESPONSE CONCURRENT WITH PSYCHOPHYSICS MEASUREMENT OF STIMULATING DEVICE RECIPIENT

(75) Inventors: Bastiaan van Dijk, Mechelen (BE); Andrew M. Botros, Maroubra (AU)

(73) Assignee: Cochlear Limited, Lane Cove (AU)

( * ) Notice: Subject to any disclaimer, the term of this patent is extended or adjusted under 35 U.S.C. 154(b) by 610 days.

(21) Appl. No.: 11/555,219

(22) Filed: Oct. 31, 2006

(65) Prior Publication Data

US 2007/0112395 A1    May 17, 2007

Related U.S. Application Data

(60) Provisional application No. 60/731,253, filed on Oct. 31, 2005.

(51) Int. Cl.
*A61N 1/00* (2006.01)
(52) U.S. Cl. ...................................................... 607/57
(58) Field of Classification Search .................. 607/55, 607/137, 57; 600/379
See application file for complete search history.

(56) References Cited

U.S. PATENT DOCUMENTS

| 452,003 | A | 5/1891 | Lipe |
|---|---|---|---|
| 3,043,000 | A | 7/1962 | Hatfield |
| D227,118 | S | 6/1973 | Muraoka |
| 3,771,685 | A | 11/1973 | Micallef |
| 4,003,521 | A | 1/1977 | Hess |
| 4,114,627 | A | 9/1978 | Lewyn et al. |
| 4,226,164 | A | 10/1980 | Carter |
| 4,240,428 | A | 12/1980 | Akhavi |
| 4,305,396 | A | 12/1981 | Wittkampf et al. |
| 4,343,312 | A | 8/1982 | Cals et al. |

(Continued)

FOREIGN PATENT DOCUMENTS

EP    0282336 A2    9/1988

(Continued)

OTHER PUBLICATIONS

Abbas et al., "Electrically Evoked Compound Action Potentials Recorded from Subjects Who Use the Nucleus CI24M Device," Ann. Otol. Rhinol. Laryngol. Suppl.; Dec. 2000; 185: pp. 6-9.

(Continued)

*Primary Examiner*—George Manuel
*Assistant Examiner*—Robert N Wieland
(74) *Attorney, Agent, or Firm*—Kilpatrick Stockton LLP

(57) ABSTRACT

The automatic measurement of evoked compound action potential (ECAP) thresholds of the auditory nerve; that is, a neural response, concurrently with the performance of psychophysics measurements of a prosthetic hearing implant recipient. During the fitting process, a stimulus signal comprising two components is applied to each stimulation channel. One signal component is configured to elicit an ECAP neural response, referred to herein as a neural response signal component. The other component is configured to elicit a response to a psychophysics stimulation, referred to herein as a psychophysics signal component. Indications of the psychophysics measurement and the concurrently obtained neural response measurements are provided to the user. For the psychophysics measurement, this includes the selected characteristics of the psychophysics signal component since the results of the applied stimulation is a recipient behavioral or auditory response.

19 Claims, 6 Drawing Sheets

U.S. PATENT DOCUMENTS

| | | |
|---|---|---|
| D267,541 S | 1/1983 | Kanemitsu |
| 4,373,531 A | 2/1983 | Wittkampf et al. |
| 4,414,701 A | 11/1983 | Johnson |
| 4,532,930 A | 8/1985 | Crosby et al. |
| 4,543,956 A | 10/1985 | Herscovici |
| 4,610,621 A | 9/1986 | Taber et al. |
| 4,731,718 A | 3/1988 | Sheu |
| 4,895,152 A | 1/1990 | Callaghan et al. |
| 4,917,504 A | 4/1990 | Scott et al. |
| 4,920,679 A | 5/1990 | Sarles et al. |
| 5,014,592 A | 5/1991 | Zweig et al. |
| 5,016,280 A | 5/1991 | Engebretson et al. |
| 5,034,918 A | 7/1991 | Jeong |
| 5,172,690 A | 12/1992 | Nappholz et al. |
| 5,278,994 A | 1/1994 | Black et al. |
| D348,067 S | 6/1994 | Lucey et al. |
| 5,565,503 A | 10/1996 | Garcia et al. |
| 5,626,629 A | 5/1997 | Faltys et al. |
| 5,674,264 A | 10/1997 | Carter et al. |
| 5,758,651 A | 6/1998 | Nygard et al. |
| 5,775,652 A | 7/1998 | Crawshaw et al. |
| 5,785,477 A | 7/1998 | McGuffey et al. |
| 5,895,416 A | 4/1999 | Barreras, Sr. et al. |
| 5,963,904 A | 10/1999 | Lee et al. |
| 5,971,334 A | 10/1999 | Crawshaw et al. |
| 5,999,856 A | 12/1999 | Kennedy |
| 6,035,001 A | 3/2000 | Eklund et al. |
| 6,044,162 A | 3/2000 | Mead et al. |
| 6,073,973 A | 6/2000 | Boscaljon et al. |
| 6,151,400 A | 11/2000 | Seligman |
| 6,157,861 A * | 12/2000 | Faltys et al. .................. 607/57 |
| 6,205,360 B1 | 3/2001 | Carter et al. |
| 6,428,484 B1 | 8/2002 | Battmer et al. |
| 6,430,402 B1 | 8/2002 | Agahi-Kesheh |
| 6,463,328 B1 | 10/2002 | John |
| 6,537,200 B2 | 3/2003 | Leysieffer et al. |
| 6,571,676 B1 | 6/2003 | Folsom et al. |
| 6,575,894 B2 | 6/2003 | Leysieffer et al. |
| 6,600,955 B1 | 7/2003 | Zierhofer |
| 6,697,674 B2 | 2/2004 | Leysieffer |
| 6,751,505 B1 | 6/2004 | Van Den Honert et al. |
| 6,892,092 B2 | 5/2005 | Palreddy et al. |
| 2001/0049466 A1 | 12/2001 | Leysieffer et al. |
| 2004/0098063 A1 | 5/2004 | Goetz |
| 2005/0004627 A1 | 1/2005 | Gibson et al. |
| 2005/0101878 A1 | 5/2005 | Daly et al. |
| 2005/0245991 A1 | 11/2005 | Faltys et al. |

FOREIGN PATENT DOCUMENTS

| | | |
|---|---|---|
| GB | 414579 | 8/1934 |
| GB | 2266045 | 10/1993 |
| WO | 9210134 | 6/1992 |
| WO | 9324176 | 12/1993 |
| WO | 9414376 | 7/1994 |
| WO | 9501709 | 1/1995 |
| WO | 9612383 | 4/1996 |
| WO | 9709863 | 3/1997 |
| WO | 9748447 | 12/1997 |
| WO | 0076436 | 12/2000 |
| WO | 0113991 | 3/2001 |
| WO | 02082982 | 10/2002 |
| WO | 03070322 | 8/2003 |
| WO | 2004021885 | 3/2004 |

OTHER PUBLICATIONS

Abbas et al., "Summary of Results Using the Nucleus CI24M Implant to Record the Electrically Evoked Compound Action Potential," Ear and Hearing, vol. 20(1), Feb. 1999, pp. 45-59.

Baumgarte, et al., "A Nonlinear Psychoacoustic Model Applied to the ISO MPEG Layer 3 Coder," Proc. 99th Conv. Aud. Eng. Soc., New York, NY, Oct. 1995, preprint 4087.

Brown et al., "Electrically Evoked Whole-Nerve Action Potentials: Data from Human Cochlear Implant Users," Journal of Acoustical Society of America, Sep. 1990, pp. 1385-1391.

Brown et al., "The Relationship Between EAP and EABR Thresholds and Levels Used to Program the Nucleus 24 Speech Processor: Data from Adults," Ear and Hearing, Apr. 2000, pp. 151-163, vol. 21(2).

Charasse, et al., "Automatic analysis of auditory nerve electrically evoked compound action potential with an artificial neural network," Artificial Intelligence in Medicine (2004) 31, pp. 221-229.

Charasse, et al., "Comparison of Two Different Methods to Automatically Classify Auditory Nerve Responses Recorded with NRT System," Acta Acustica United with Acustica, vol. 90 (2004), pp. 512-519.

Cohen et al., "Spatial spread of neural excitation in cochlear implant recipients: comparison of improved ECAP method and psychophysical forward masking," Hearing Research, 179 (2003), pp. 72-87.

Cohen et al., "Spatial spread of neural excitation: comparison of compound action potential and forward-masking data in cochlear implant recipients," International Journal of Audiology 2004, 43, pp. 346-355.

Delgado et al., "Automated Auditory Brainstem Response Interpretation," IEEE Engineering in Medicine and Biology, Apr./May 1994, pp. 227-237.

Dijk et al., "Development of a prototype fully-automated intra-operative ECAP recording tool, using NRT(TM) v3," 2003 Conference on Implantable Auditory Prostheses, 2003, 7 pages total.

Dillier et al., "Measurement of the Electrically Evoked Compound Action Potential via a Neural Response Telemetry System," Annals of Otology, Rhinology & Laryngology, vol. 111, No. 5, May 2002, pp. 407-414.

Edler, et al., "ASAC-Analysis/Synthesis Audio Codec for Very Low Bit Rates," Proc. 100th Conv. Aud. Eng. Soc., May 1996, preprint 4179.

European Search Report (Annex), EP 01 95 9971, dated Aug. 2, 2005.

Franck et al., "Estimation of Psychophysical Levels Using the Electrically Evoked Compound Action Potential Measured with the Neural Response Telemetry Capabilities of Cochlear Corporation's CI24M Device," Ear & Hearing, 2001, pp. 289-299.

Franck, "A Model of a Nucleus 24 Cochlear Implant Fitting Protocol Based on the Electrically Evoked Whole Nerve Action Potential," Ear & Hearing, 2002, pp. 67S-71S.

Hartmann et al., "Evoked Potentials from the Auditory Nerve Following Sinusoidal Electrical Stimulation of the Cochlea: New Possibilities for Preoperative Testing in Cochlear-Implant Candidates?" Acta Otoloaryngol (Stockh) 1994,114, pp. 495-500.

Hughes et al., "Comparison of EAP Thresholds with MAP Levels in the Nucleus 24 Cochlear Implant: Data from Children," Ear and Hearing, vol. 21 (2), Apr. 2000, pp. 164-174.

International Preliminary Examination Report, PCT/AU01/01032, dated Apr. 10, 2002.

International Preliminary Examination Report, PCT/AU02/00500, dated Feb. 12, 2003.

International Search Report and Written Opinion, PCT/US05/21207 dated Feb. 8, 2006.

International Search Report, PCT/AU01/01032, dated Oct. 5, 2001.

International Search Report, PCT/AU02/00500, dated Jun. 26, 2002.

Lai et al., "A Simple Two-Component Model of the Electrically Evoked Compound Action Potential in the Human Cochlea," Audiology & Neuro—Otology, Nov./Dec. 2000; 5: pp. 333-345.

Miller et al., "An Improved Method of Reducing Stimulus Artifact in the Electrically Evoked Whole-Nerve Potential," Ear & Hearing, 2000, pp. 280-290.

Nicolai et al., Performance of Automatic Recognition Algorithms in Nucleus Neural Response Telemetry (NRT (TM)), 2003 Conference on Implantable Auditory Prostheses, 2003, one page total.

Seyle, et al., "Speech Perception Using Maps Based on Neural Response Telemetry Measures," Ear & Hearing, 2002, pp. 72S-79S.

Smoorenburg et al., "Speech Perception in Nucleus CI24M Cochlear Implant Users wtih Processor Settings Based on Electrically Evoked Compound Action Potential Thresholds," Audiology & Neuro—Otology, Nov./Dec. 2002; 7: pp. 335-347.

Supplementary Partial European Search Report, EP 02 71 7863 dated Oct. 18, 2005.

Thai-Van et al., "Modeling the Relationship Between Psychophysical Perception and Electrically Evoked Compound Action Potential Threshold in Young Cochlear Implant Recipients: Clinical Implications for Implant Fitting," Cinical Neurophysiology 115 (2004), pp. 2811-2824.

Vannier et al., "Objective detection of brainstem auditory evoked potentials with a priori information from higher presentation levels," Artificial Intelligence in Medicine 25 (2002), pp. 283-301.

* cited by examiner

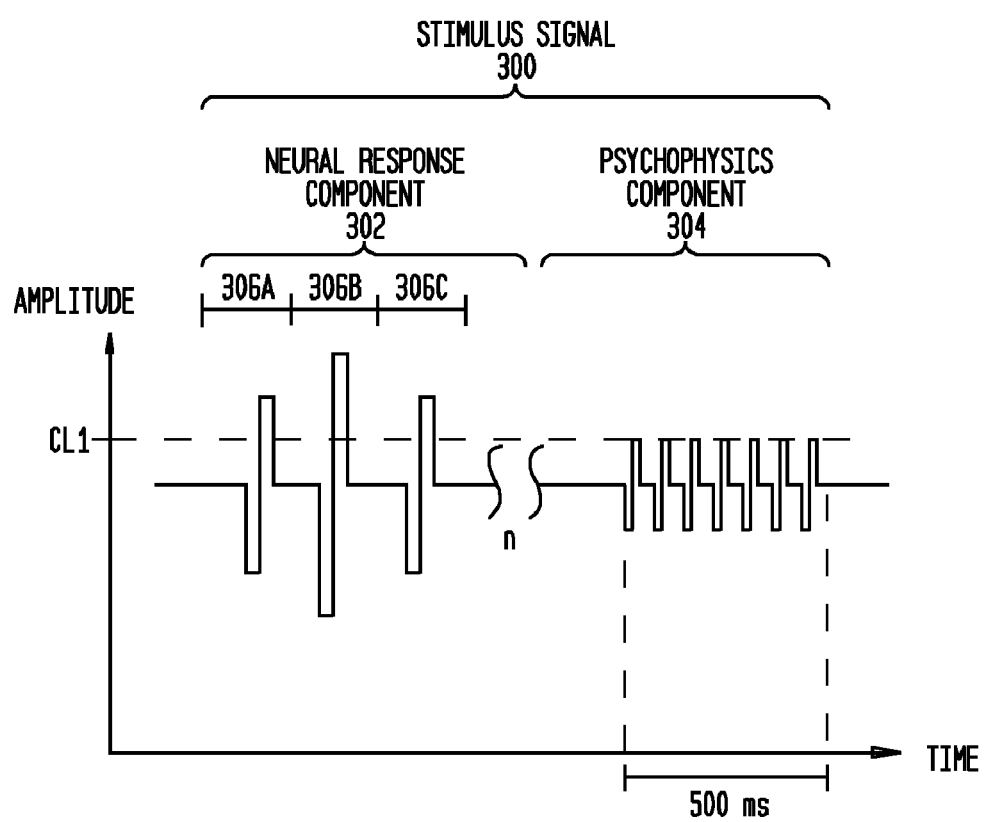

AUTOMATIC MEASUREMENT OF NEURAL RESPONSE CONCURRENT WITH PSYCHOPHYSICS MEASUREMENT OF STIMULATING DEVICE RECIPIENT

CROSS-REFERENCE TO RELATED APPLICATIONS

The present invention claims priority from U.S. Provisional Patent Application 60/731,253, filed on Oct. 31, 2005, which is hereby incorporated by reference herein in its entirety.

BACKGROUND

1. Field of the Invention

The present invention relates generally to configuring a stimulating medical device to a recipient and, more particularly, to the automatic measurement of neural response concurrent with psychophysics measurement of stimulating device recipients.

2. Related Art

Determining the response of an auditory nerve to stimulation has been addressed with limited success in conventional systems. Typically, following the surgical implantation of a prosthetic hearing implant, the implant is customized to conform to the specific recipient's needs. This process of configuring an implanted hearing prosthesis for a particular recipient is commonly referred to as "fitting" the implant to the recipient. This fitting process involves the collection and determination of recipient-specific parameters such as threshold levels (T levels) and comfort levels (C levels) for each stimulation channel using psychophysics. This collection of patient-specific parameters, including the T and C levels for plurality of stimulation channels, is commonly referred to as a MAP.

Essentially, a clinician performs psychophysics measurements by applying stimulation pulses for each channel and subjectively interpreting a behavioral indication from the implant recipient as to the threshold and comfort levels of the perceived sound. For implants with a large number of stimulation channels this process is quite time consuming and rather subjective as it relies heavily on the recipient's subjective impression of the stimulation rather than an objective measurement. Also, the psychophysics approach is further limited in the cases of children, infants and prelingually or congenitally deaf recipients who are unable to provide an accurate impression of the resultant hearing sensation. Hence the fitting of the implant may be sub-optimal and may directly hamper the speech and hearing development of recipients.

SUMMARY

In accordance with one aspect of the invention, an apparatus for fitting a cochlear implant for a recipient is disclosed, the apparatus configured to automatically measure evoked compound action potential (ECAP) thresholds of the recipient's auditory nerve concurrently with the performance of psychophysics measurements of the cochlear implant recipient.

In accordance with another aspect of the invention, a method for fitting a cochlear implant for a recipient is disclosed, the method comprising: applying to each stimulation channel of the cochlear implant a stimulus signal comprising a neural response component and a psychophysics signal component; automatically measuring an evoked compound action potential (ECAP) generated in response to the application of the neural response component; providing a user an indication of the psychophysics measurement and the concurrently obtained neural response measurements.

BRIEF DESCRIPTION OF THE DRAWINGS

Embodiments of the present invention are described herein in conjunction with the accompanying drawings, in which:

FIG. 3 is a stimulus graph of a two-component stimulus signal used in accordance with an embodiment of the present invention.

DETAILED DESCRIPTION

Figure 1A:
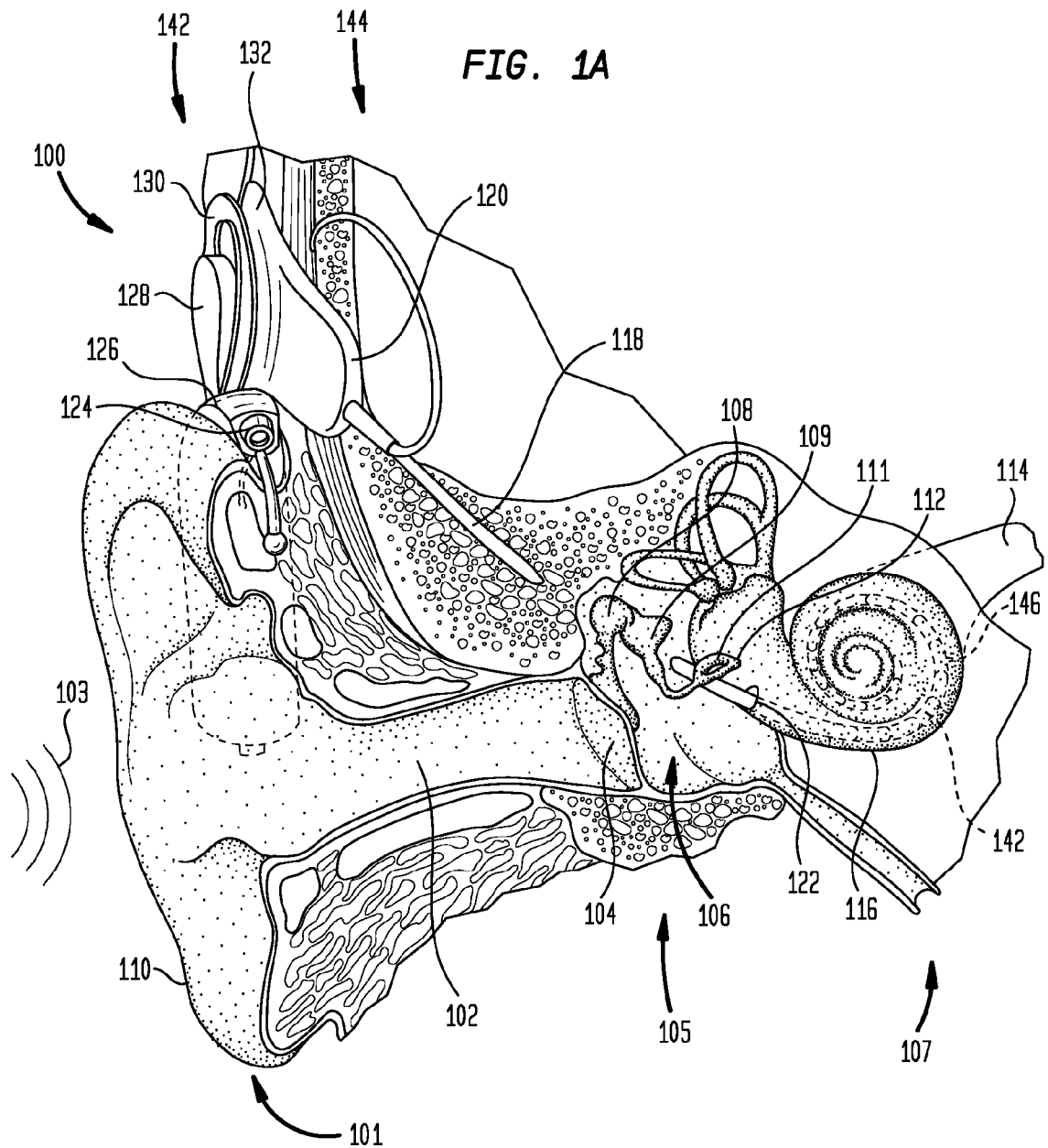
FIG. 1A is a schematic diagram of a prosthetic hearing implant implanted in a recipient.

Embodiments of the present invention are generally directed to the automatic measurement of evoked compound action potential (ECAP) thresholds of the auditory nerve; that is, a neural response, concurrently with the performance of psychophysics measurements of a prosthetic hearing implant recipient. As noted, psychophysics measurements are performed to establish patient-specific parameters (such as threshold and comfort levels) for each of a plurality of stimulation channels.

During the fitting process, a stimulus signal comprising two components is applied to each stimulation channel. One signal component is configured to elicit an ECAP neural response, referred to herein as a neural response signal component. The other component is configured to elicit a response to a psychophysics stimulation, referred to herein as a psychophysics signal component. There is no particular relationship between the neural response and psychophysics signal components. For example, the neural response signal component may precede or follow the psychophysics signal component, the time duration of the neural response signal component may be greater than or less than that of the psychophysics signal component, and so on.

In certain embodiments, indications of the psychophysics measurement and the concurrently obtained neural response measurements are provided to the user. For the psychophysics measurement, this includes the selected characteristics of the psychophysics signal component since the results of the applied stimulation is a recipient behavioral or auditory response.

This enables the neural response measurements to be used as an objective basis to judge the subjective determinations of the concurrently-determined psychophysics measurements. This may increase the clinician's confidence in executing the fitting process, facilitating the efficient creation of the recipient MAP. Such advantages are attained with minimal drawbacks. The neural response stimulus is neither perceivable by the recipient nor does it interfere with the psychophysics measurements. Furthermore, the neural response measurements are performed automatically and without clinician involvement. Thus, the concurrence performance of neural response measurements occurs in the background during the performance of psychophysics measurements.

Exemplary embodiments of the present invention are further described below in conjunction with the implanted component of a cochlear implant, such as a Contour™, Freedom™, Nucleus™ or Cochlear™ implant sold by Cochlear Limited, Australia. Such devices are described in U.S. Pat. Nos. 4,532,930, 6,537,200, 6,565,503, 6,575,894, and 6,697,674, the entire contents and disclosures of which are hereby incorporated by reference herein. It should be understood to those of ordinary skill in the art that embodiments of the present invention may be used in other prosthetic hearing implants and, more generally, in other stimulating medical devices such as neurostimulators, cardiac pacemakers, defibrillators, etc.

FIG. 1 is a cut-away view of the relevant components of outer ear 101, middle ear 105 and inner ear 107, which are described next below. In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to acoustic wave 103. This vibration is coupled to oval window or fenestra ovalis 112 through three bones of middle ear 105, collectively referred to as the ossicles 106 and comprising the malleus 108, the incus 109 and the stapes 111.

Bones 108, 109 and 111 of middle ear 105 serve to filter and amplify acoustic wave 103, causing oval window 112 to articulate, or vibrate. Such vibration sets up waves of fluid motion within cochlea 116. Such fluid motion, in turn, activates tiny hair cells (not shown) that line the inside of cochlea 115. Activation of the hair cells causes appropriate nerve impulses to be transferred through the spiral ganglion cells and auditory nerve 114 to the brain (not shown), where they are perceived as sound. In deaf persons, there is an absence or destruction of the hair cells. Prosthetic hearing implant 100 is utilized to directly stimulate the ganglion cells to provide a hearing sensation to the recipient.

FIG. 1 also shows how an implanted prosthetic hearing implant 120 is positioned in relation to outer ear 101, middle ear 105 and inner ear 107. Prosthetic hearing implant 120 comprises external component assembly 142 which is directly or indirectly attached to the body of the recipient, and an internal component assembly 144 which is temporarily or permanently implanted in the recipient. External assembly 142 comprises microphone 124 for detecting sound which is outputted to a BTE (Behind-The-Ear) speech processing unit 126 that generates coded signals and are provided to an external transmitter unit 128, along with power from a power source such as a battery (not shown).

External transmitter unit 128 comprises an external coil 130 and, preferably, a magnet (not shown) secured directly or indirectly to external coil 130. Internal components 144 comprise an internal receiver unit 132 having an internal coil (not shown) that receives and transmits power and coded signals from external assembly 142 to a stimulator unit 120 to apply the coded signal along an electrode assembly 118. Electrode assembly 118 enters cochlea 116 at cochleostomy region 122 and has one or more electrodes 142 positioned to substantially be aligned with portions of tonotopically-mapped cochlea 116. Signals generated by stimulator unit 120 are applied by electrodes 142 to cochlea 116, thereby stimulating auditory nerve 114. It should be appreciated that although in the embodiment shown in FIG. 1 electrodes 142 are arranged in an array 146, other arrangements are possible.

Figure 1B:
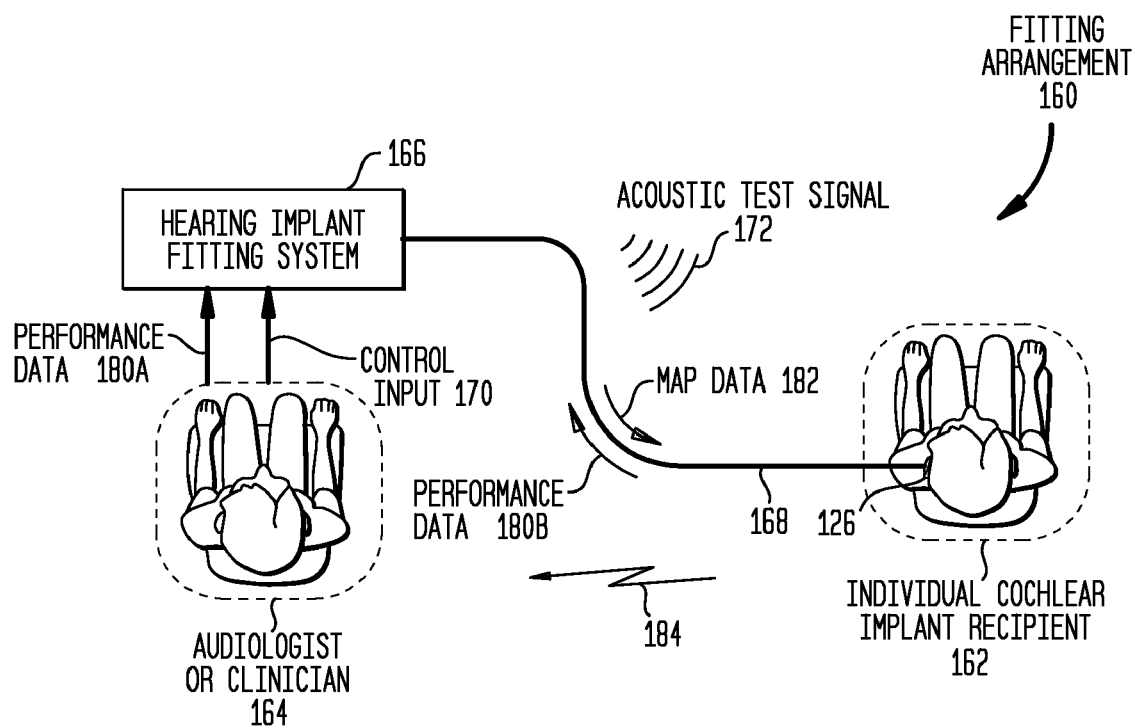
FIG. 1B is a schematic diagram illustrating one exemplary cochlear implant fitting arrangement configured to fit a cochlear implant to a recipient.

The effectiveness of a prosthetic hearing implant is dependent not only on the device itself but also on the way in which the device is configured or "fit" for the recipient. Fitting of a device, also referred to as "programming" or "mapping," creates a set of instructions that defines the specific characteristics used to stimulate electrodes 142 of the implanted array 146. This set of instructions is referred to as the recipient's "program" or "MAP." FIG. 1B is a schematic diagram illustrating one exemplary arrangement 160 in which a fitting system 166 is utilized to fit cochlear implant 100 to a recipient 162. Fitting System 166 performs one or more of the functions of mapping, neural response measuring, acoustic stimulating, and recording of neural response measurements and other stimuli. As one of ordinary skill in the art would appreciate, the characteristics and code transmitted by cochlear implant 100 are dependent in part on the effectiveness with which the implant is fit to an individual recipient 162.

As shown in FIG. 1B, an audiologist or clinician 164 uses a hearing implant fitting system 166 ("fitting system" herein) comprising interactive software and computer hardware to create individualized recipient map data 182 that are digitally stored on system 166 and ultimately downloaded to the memory of speech processor 126 of recipient 162. System 166 is programmed and/or implements software programmed to carry out one or more of the functions of mapping, neural response measuring, acoustic stimulating, and recording of neural response measurements and other stimuli.

In the embodiment illustrated in FIG. 1B, speech processor 126 of cochlear implant 100 is connected directly to fitting system 166 to establish a data communication link 168 between the speech processor and fitting system. System 166 is thereafter bi-directionally coupled by means of data communication link 168 with speech processor 126. It should be appreciated that although speech processor 126 and fitting system 166 are connected via a cable in FIG. 1B, any communications link now or later developed may be utilized to communicably couple the implant and fitting system.

Once cochlear implant 100 is calibrated, specific mapping data 182 is determined. The particular details of the implemented fitting process are specific to the recipient, cochlear implant manufacturer, cochlear implant device, etc. As a result, only selected exemplary mapping data are described herein for clarity.

Today, most cochlear implants require at least two values to be set for each stimulating electrode 142. These values are referred to as the Threshold level (commonly referred to as the "THR" or "T-level;" "threshold level" herein) and the Maximum Comfortable Loudness level (commonly referred to as the Most Comfortable Loudness level, "MCL," "M-level," or "C;" simply "comfort level" herein). Threshold levels are comparable to acoustic threshold levels; comfort levels indicate the level at which a sound is loud but comfortable. It should be appreciated that although the terminology and abbreviations are device-specific, the general purpose of threshold and comfort levels is common among all cochlear implants: to determine a recipient's electrical dynamic range.

In adult cochlear implant patients, threshold and comfort levels are typically measured using verbal feedback from recipient 162. For children, who often lack the listening experience, language, or conceptual development to perform specific fitting tasks, audiologists and clinicians must often rely on clinical intuition and trial and error to appropriately estimate comfort levels for young recipients. The above and other feedback is generally referred to by reference numeral 184 in FIG. 1B. Performance data provided directly to fitting system 166 may be provided via data connection 168 as performance data 180B, while performance data provided by the audiologist/clinician based on oral feedback or observations 184 is shown in FIG. 1B as performance data 180A (performance data 180A and 180B are generally and collectively referred to herein as performance data 180).

In carrying out embodiments of the present invention, fitting system 166 sends an acoustic stimulus to instruct speech processor 126 to provide electrodes 142 with a stimulus comprising two components: a stimulus component for generating an ECAP neural response, and a stimulus component for generating a psychophysics response. The electrical activity of the nerves in cochlea 116 which are evoked in response to the stimulation, i.e. the neural response, is then detected, encoded and transmitted back to fitting system 166. In one embodiment, fitting system 166 processes the neural response data using commonly available neural response measurement software.

Embodiments of the present invention use machine learning to create the decision making algorithm that analyzes the traces of the transmitted data and makes a decision on whether or not the trace includes a neural response, and the strength of the response. In some embodiments, the concurrently-measured neural response; that is, the Evoked Compound Action Potential (ECAP), may be indicated, visually and/or audibly, concurrently and in combination with the psychophysics mapping.

The psychophysics burst will produce a stimulation that will allow the recipient to react and in turn allow the clinician to map the T and C levels using fitting system 166. Psychophysics is an approach to understanding perception that relates the characteristics of physical stimuli to attributes of the sensory experience such stimuli produce. In the exemplary application of a cochlear implant, the term"psychophysics" refers to the study of the perceptions elicited in recipients by electrical stimulation of the auditory nerve. Typically, a clinician observes a recipient that receives an electrical stimulation and judges the type of response. For example, a stimulus pulse of 100 microamps may be inaudible to the recipient, 200 microamps may be perceived by the recipient as a soft sound, and 500 microamps may be perceived by the recipient as a sound that is too loud. This is such a distinct sensation that it is possible to convey a melody to a recipient by varying the stimuli amplitude and thus observe a change in behavior of the recipient.

A neural response telemetry device is a computerized system that allows for measurement of the Evoked Compound Action Potential (ECAP) response of the auditory nerve evoked by electrical stimulation applied by electrodes implanted in the cochlea. As such, neural response telemetry allows a clinician to set a MAP that does not rely on subjective observations. Such a system is in clinical use by practitioners for adjustment of prosthetic hearing implants. A particular advantage of neural response telemetry is that it does not require the recipient to pay attention or remain immobile, which notably allows for use with infants. Types of neural response telemetry are described in U.S. Pat. Nos. 6,915,166 and 5,758,651, which are hereby incorporated by reference herein in their entirety. One exemplary computerized system that uses neural response telemetry is the Nucleus® NRT™ 3.0, commercially available from Cochlear Limited, Australia.

However, based on observations, the inventors have concluded that traditional neural response telemetry may be subject to a number of drawbacks. First, the clinician must obtain a neural response curve so as to be able to measure the amplitude of the neural response. To obtain such a response curve, a certain number of parameters related to measurement, in particular the response acquisition latency, the amplification gain, the stimulation voltage, etc., must be adjusted and optimized. These initial operations are time consuming, subjective, and the results strongly depend on the skill of the clinician. Second, when the response curves that allow for plotting of the growth function for an electrode have been obtained, the clinician must determine which of these curves can be used and which cannot. In particular, some response curves have a poor signal-to-noise ratio and are not easily identifiable. This selection is also subjective, and the results directly influence the subsequent adjustment of the implant. Third, clinicians must measure the voltages of the peaks on each response curve, to determine the response amplitude. This measurement, which is also subjective, directly influences the adjustment of the implant, and is also a lengthy and bothersome procedure. More importantly, the subjective determinations necessary for neural response telemetry may decrease its objective reliability.

Some clinicians using neural response measurements alone may experience the difficulties as discussed above, and thus may be reluctant to use systems such as Nucleus NRT. Embodiments of the present invention may eliminate or reduce this reluctance by using a neural response measurement in the background; that is, automatically, when the MAP is created. The background ECAP or neural response measurement does not impact the speed or accuracy using the standard psychophysics mapping procedure. Advantageously, clinicians may develop judgment and become accustomed to neural response measurements by using automatic and concurrent neural response measurements along with the psychophysics. Still further, automatic and concurrent neural response measurements may provide additional objective information to expedite the fitting process. Thus, with children recipients, for example, when the threshold-NRT is very close to the behavioral threshold, a clinician using embodiments of the present invention would not over-stimulate the recipient leading to sub-optimal performance. Another advantage of embodiments of the present invention is that automated fitting may be achieved and be accepted by clinicians.

To provide for such measurements, an exemplary system of the present invention may comprise a prosthetic hearing implant with a neural response measurement system and recordal capabilities, software to drive the appropriate stimulus and an acoustic stimulator as shown in FIG. 1.

An exemplary embodiment of a two-component stimulus signal generated in accordance with the teachings of the present invention is shown in FIG. 3. The two-component stimulus signal 300 comprises a neural response stimulus signal component 302 and a psychophysics stimulus signal component 304.

As shown in FIG. 3, psychophysics stimulus signal component 304 comprises a series of pulses, collectively referred to as a psychophysics burst each having a period of 1/map stimulation rate. Neural response stimulus signal component 302 comprises a series of pulses each having a period of 1/neural response stimulation rate.

The neural response stimulation rate may be greater or less than the psychophysics stimulation rate. In one embodiment, on a single stimulation channel neural response stimulation rate is measured approximately 80 Hz, and the psychophysics response is measured at a higher rate, referred to as the map rate. In one embodiment, the map rate is approximately 5000 Hz.

Psychophysics stimulus signal component 304 may be at the current level CL1 and each pulse of the neural response stimulation signal component 302 may have an amplitude of greater than CL1. It should be appreciated, however, that the relative and absolute amplitude of the pulses of neural response stimulation signal component 302 and psychophysics stimulation signal component 304 may be different in other embodiments of the present invention.

Neural response stimulation signal component 302 has three buffers, 306A, 306B and 306C. Each buffer 306 may be repeated n times. For example using forward masking paradigm, 5 neural response measurements may be suitable for each buffer and would be repeated 5 times for a total of 15 frames before psychophysics burst 304.

Because the psychophysics burst rate is much higher than the rate of neural response signal 302 (on the average of 900 to 122 Hz), neural response measurement signal 302 will hardly influence the loudness percept, since psychophysics burst 304 will sound much louder. The different in loudness percept may ensure that both T and C level estimates will be based on the psychophysics burst and not on the neural response recording.

Additional variations the parameters of two-component stimulus signal 300 are readily envisaged by the embodiments of the present invention. The clinician may set the parameters based on experience or using the default parameter set by the software. In particular, psychophysics burst 304 may be alternated depending on the current level, channel of stimulation and recipient.

Figure 2A:
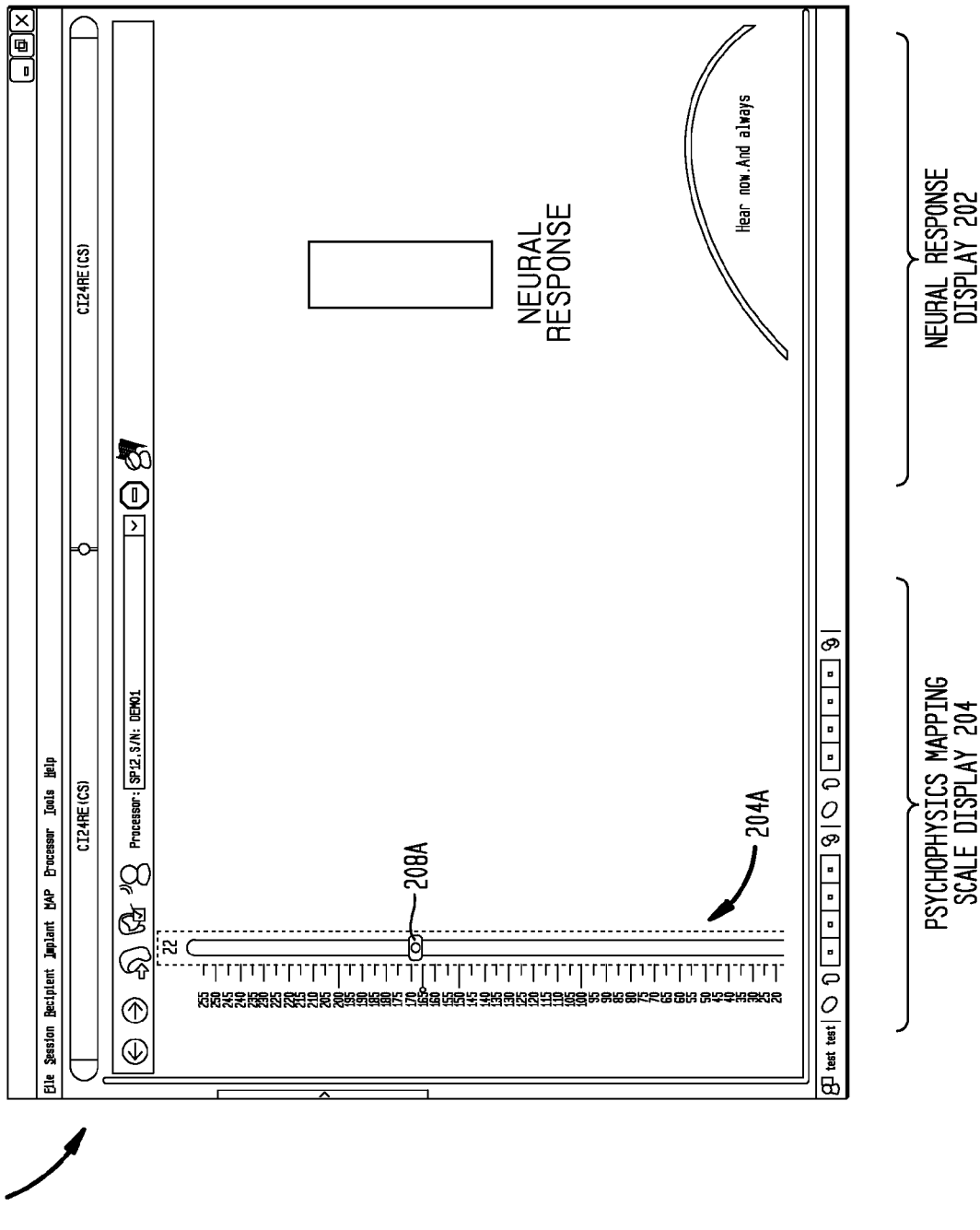
FIG. 2A is a display providing an indication of a concurrent measurement of evoked compound action potential (ECAP) and psychophysics response in accordance with one embodiment of the present invention.
Figure 2B:
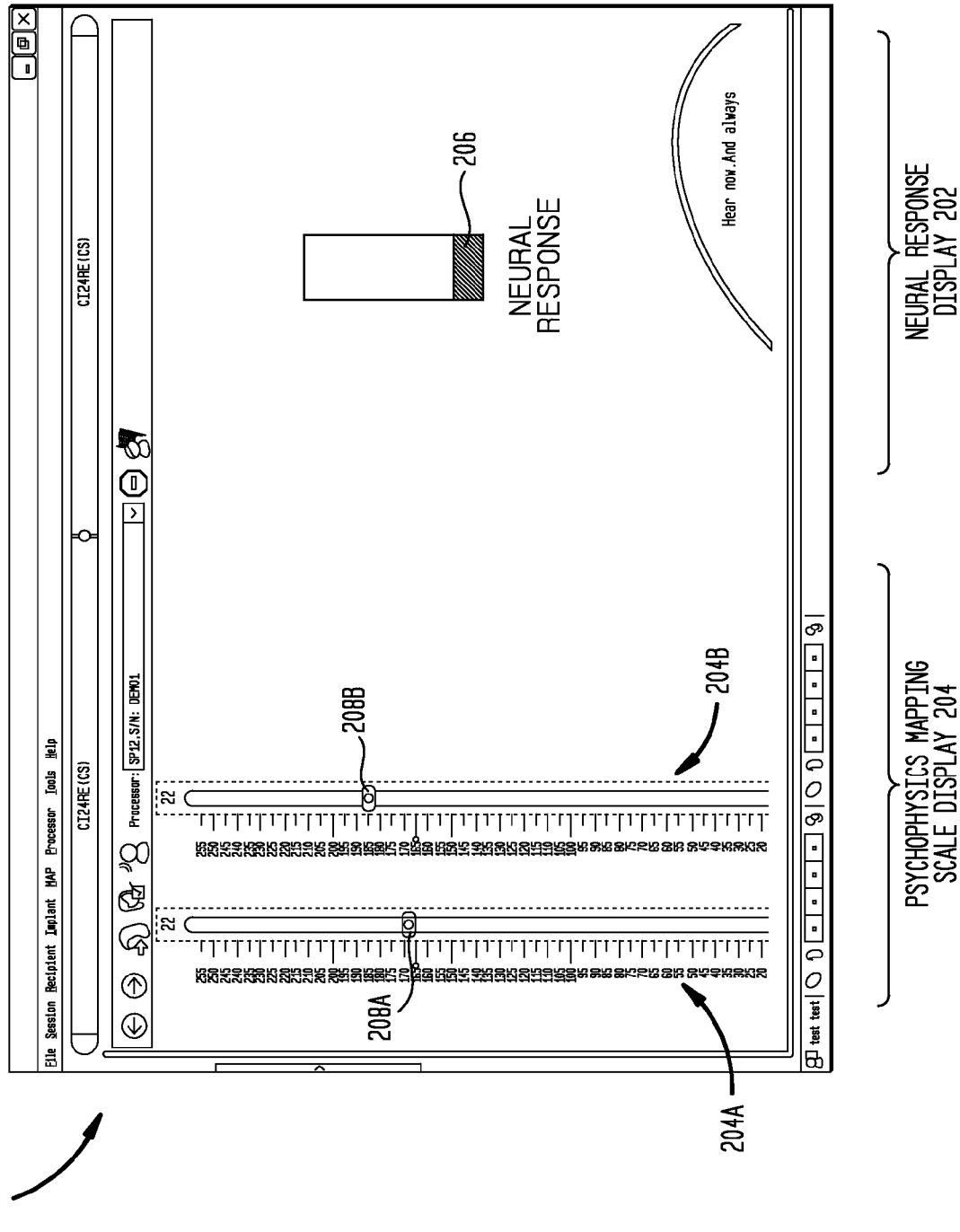
FIG. 2B is a display providing an indication of a concurrent measurement of evoked compound action potential (ECAP) and psychophysics response in accordance with one embodiment of the present invention.
Figure 2C:
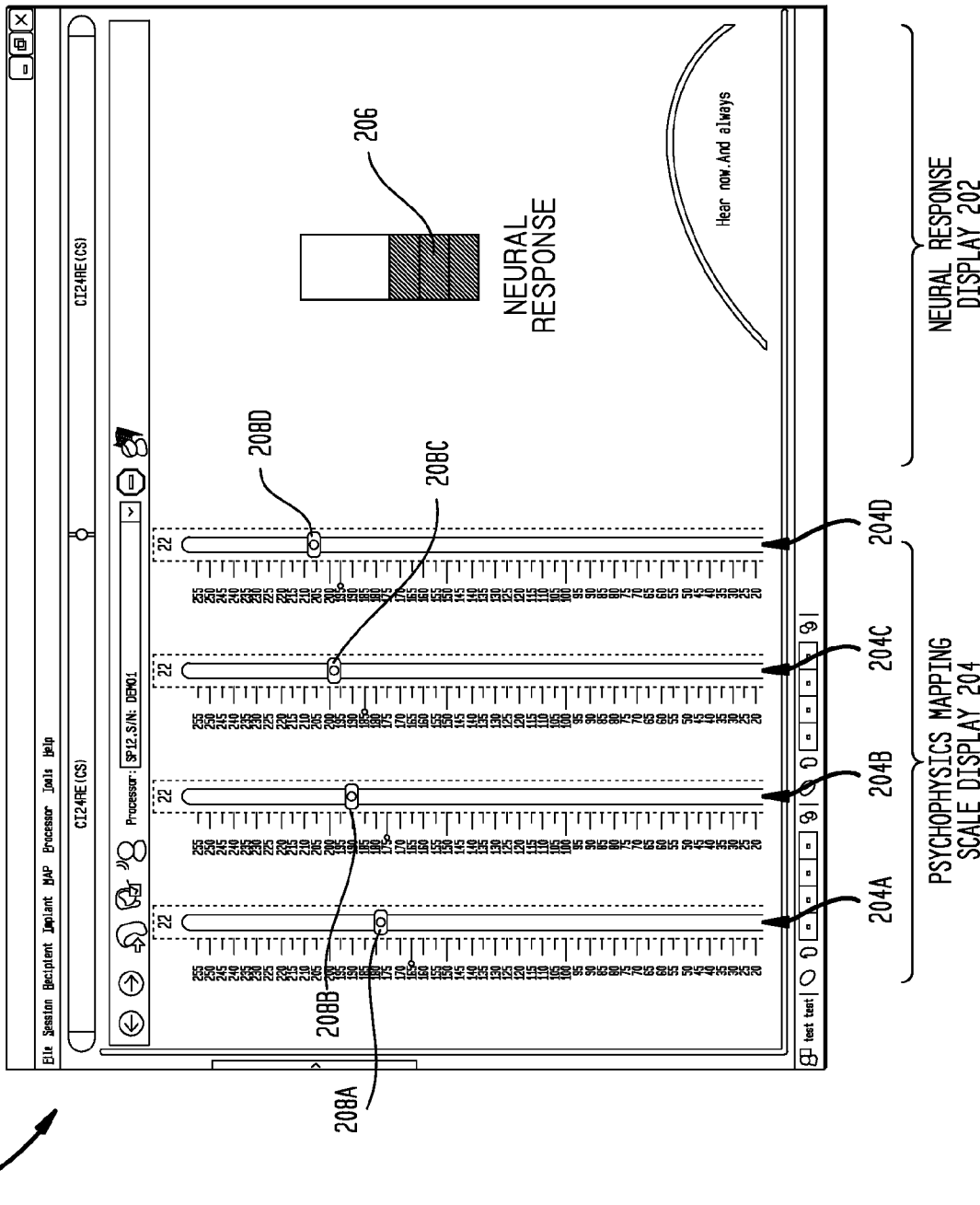
FIG. 2C is a display providing an indication of a concurrent measurement of evoked compound action potential (ECAP) and psychophysics response in accordance with one embodiment of the present invention.

FIGS. 2A, 2B and 2C are displays generated by an embodiment of the present invention. Each display 200A, 200B and 200C providing concurrent presentation, in a visual form, of an indication of an evoked neural response or ECAP measurement and the applied psychophysics mapping scale. Each display 200 includes a neural response display 202 in which the measured ECAP is displayed, and a psychophysics mapping scale display 204 in which the applied psychophysics mapping scale is displayed. In this illustrative embodiment, the strength of the neural response is displayed using a linear strength indicator 206. In addition, an audible signal (not shown) may be beneficial when a clinician is observing a recipient's behavior and not watching display 200. Display 200 enables a clinician to concurrently evaluate the T and C thresholds on a channel set by psychophysics in combination with an indication of the neural response of the same auditory nerve.

Generally, the systems, methods, techniques and approaches of the present invention apply electrical stimulation to a target neural region at incrementally greater current levels beginning with an initial current level that is below to a typical threshold neural response level; record a neural response measurement of an auditory signal which is generated by the target neural region in response to the stimulation; and determine whether the neural response measurement contains a neural response based on a plurality of features extracted from the auditory signal. In one embodiment, the expert system may be built using the induction of decision trees as disclosed in PCT Application No. PCT/US05/21204 (Attorney Docket COCH-0153-PCT), entitled "Automatic Determination of the Threshold of an Evoked Neural Response," the entire contents and disclosure of which is hereby incorporated by reference herein. In one implementation of such an embodiment, the induction of decision trees machine learning algorithm is the algorithm C5.0 described in Quinlan, J., 1993. "C4.5: Programs for Machine Learning." Morgan Kaufmann, San Mateo; and Quinlan, J., 2004. "See5: An Informal Tutorial." Rulequest Research, both of which are hereby incorporated by reference herein.

FIGS. 2A, 2B and 2C show a sequence of several screenshots 200 of one embodiment of the present invention. Each display 200A-200C shows one or more psychophysics mapping scales 204 for a stimulation channel 22 of electrode array 142. The current level (CL) is shown by a marker bar 208 on mapping scale 204. The current level may be adjusted by the clinician using a clicker, keyboard, mouse, touch screen or other user interface to move marker 208.

In FIG. 2A, a low current level stimulation is set by marker 208A on mapping scale 204A and no neural response is found as indicated by neural response strength indicator 206 in neural response display 202. This is depicted by the absence of any neural strength in linear strength indicator 206.

In FIG. 2B, a relatively higher current level is used by setting marker 208B on mapping scale 204B above the level the marker was set on mapping scale 204A. This produces a neural response as indicated by neural response strength indicator 206 in neural response display 202. This is depicted by the few bars representing the measured neural strength in linear strength indicator 206.

In FIG. 2C, a still relatively higher current level is used by setting marker 208C on mapping scale 204C above the levels for mapping scales 204A and 204B. Still further, the current level may be higher by setting marker 208D on mapping scale 204D above the levels for mapping scales 204A, 204B and 204C. This is depicted by the increase in the number of bars representing the measured neural strength in linear strength indicator 206.

Clinician may for instance, depending on recipient's response to the psychological burst, choose the current level shown by mapping scale 204B in FIG. 2B as the T level, and current level shown by mapping scale 204C as the C level for the initial MAP. In addition, assuming that the recipient responds to the current level shown in mapping scale 204A, the clinician has objective evidence that the T level may be too low since no neural response is indicated. This may prevent an improper fitting of the prosthetic hearing implant.

In the embodiments illustrated in FIGS. 2A-2C, a visual neural response indicator is implemented as a linear strength indicator 206. As one of ordinary skill in the art would appreciate, a myriad of other display elements may be utilized to visually convey the strength of the neural response. In one embodiment, for example, a series of individual display buttons or icons, with the quantity that have changed in display (color, intensity, etc.) reflecting the strength of the neural response. In other embodiments, dials, numerical values, graphs (bar graphs, line graphs, etc.), pie charts, etc., may be implemented, with location, quantity, color, intensity or other display characteristic selected to assist in the conveyance of neural response strength.

It should also be appreciated that audio indications of neural response strength may be implemented in addition to or as an alternative to the visual display noted above. Such an audio indication may include the alteration of audio characteristics to reflect neural response strength including, but not limited to, volume, quantity, tones, frequency, etc.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for fitting a cochlear implant for a recipient, comprising:
   receiving a user-specified current level;
   applying to a stimulation channel of the cochlear implant a stimulus signal comprising a substantially imperceptible neural response component based on the user-specified current level and configured to elicit an evoked compound action potential (ECAP) neural response, and a perceivable psychophysics component having the user-specified current level and configured to elicit a psychophysics response, wherein each of the neural response component and the psychophysics component are configured for determination of a common dynamic range parameter for the cochlear implant;
   automatically measuring the ECAP neural response; and
   concurrently displaying the ECAP neural response measurement and an indication of the user-specified current level.

2. The method of claim 1, wherein the dynamic range parameter is a threshold level and further comprising:
   receiving a user-specified threshold level in response to displaying the ECAP neural response measurement and the indication of the user-specified current level.

3. The method of claim 2, further comprising:
   downloading the user-specified threshold level to the cochlear implant.

4. The method of claim 2, further comprising:
   subjectively interpreting the psychophysics response in determining the dynamic range parameter.

5. The method of claim 4, wherein the user-specified threshold level is received after subjectively interpreting the psychophysics response.

6. The method of claim 4, further comprising:
   judging the subjective interpretation of the psychophysics response against the displayed ECAP neural response measurement, wherein the displayed ECAP neural response measurement provides an objective basis against which to judge the subjective interpretation of the psychophysics response.

7. The method of claim 1, wherein the dynamic range parameter is a comfort level, and wherein the method further comprises:
   receiving a user-specified comfort level in response to displaying the ECAP neural response measurement and the indication of the user-specified current level.

8. The method of claim 7, further comprising:
   downloading the user-specified comfort level to the cochlear implant.

9. The method of claim 1, wherein displaying an indication of the user-specified current level comprises displaying an applied psychophysics mapping scale.

10. The method of claim 9, wherein a marker bar indicates the user-specified current level on the applied psychophysics mapping scale.

11. The method of claim 10, further comprising:
    receiving an adjustment of the user-specified current level via a user-initiated movement of the marker bar.

12. The method of claim 1, wherein displaying the ECAP neural response measurement comprises displaying a number of bars indicative of the ECAP neural response measurement.

13. The method of claim 1, wherein the neural response component is not perceived by the recipient.

14. A fitting system configured to receive a user-specified current level, and to provide an instruction to a cochlear implant to cause the cochlear implant to apply to a stimulation channel of a cochlear implant a first stimulus signal comprising a substantially imperceptible neural response component based on the user-specified current level and configured to elicit an evoked compound action potential (ECAP) neural response, and a perceivable psychophysics component having the user-specified current level and configured to elicit a psychophysics response, wherein each of the neural response component and the psychophysics component are configured for determination of a common dynamic range parameter for the cochlear implant; and further configured to automatically measure the ECAP neural response, and to concurrently display the ECAP neural response measurement and an indication of the user-specified current level.

15. The apparatus of claim 14, wherein the neural response component comprises a series of pulses each having a first period, and the psychophysics component comprises a series of pulses each having a second period.

16. The apparatus of claim 14, wherein the fitting system comprises:
    a display comprising a neural response display and a psychophysics mapping scale display,
    wherein the neural response display is configured to display the ECAP neural response measurement; and
    wherein the psychophysics mapping scale display is configured to display a psychophysics mapping scale.

17. The apparatus of claim 16, wherein the psychophysics mapping scale display further comprises:
    a marker bar on the psychophysics mapping scale indicating the user-specified current level.

18. The apparatus of claim 14, wherein the fitting system is further configured to provide an audio indication of the ECAP neural response measurement.

19. The apparatus of claim 14, wherein the fitting system is further configured to cause the cochlear implant to apply to the stimulation channel of the cochlear implant a second stimulus signal comprising a substantially imperceptible neural response component configured to elicit an ECAP neural response, and a substantially imperceptible psychophysics component configured to elicit a psychophysics response.

* * * * *